United States Patent [19]

Williams

[11] Patent Number: 4,758,228
[45] Date of Patent: Jul. 19, 1988

[54] MEDICAL INFUSION PUMP WITH SENSORS

[75] Inventor: David R. Williams, San Diego, Calif.

[73] Assignee: Centaur Sciences, Inc., Stamford, Conn.

[21] Appl. No.: 931,506

[22] Filed: Nov. 17, 1986

[51] Int. Cl.[4] ............................................. A61M 1/00
[52] U.S. Cl. ................................... 604/153; 604/118; 604/123; 604/34; 128/DIG. 12; 417/477
[58] Field of Search ............... 604/153, 122, 123, 118, 604/121, 34, 250, 245; 128/D12, D13; 417/474, 476, 477

[56] References Cited

U.S. PATENT DOCUMENTS

| | | | |
|---|---|---|---|
| 3,912,168 | 10/1975 | Mullins et al. | 604/153 |
| 4,155,362 | 5/1979 | Jess | 604/123 |
| 4,187,057 | 2/1980 | Xanthopoulos | 417/477 |
| 4,210,138 | 7/1980 | Jess et al. | 417/477 |
| 4,452,599 | 6/1984 | Albisser et al. | 604/153 |
| 4,487,601 | 12/1984 | Lindemann | 604/122 |
| 4,604,090 | 8/1986 | Reinicke | 604/122 |

Primary Examiner—Dalton L. Truluck
Assistant Examiner—Denise Whelton
Attorney, Agent, or Firm—Chilton, Alix & Van Kirk

[57] ABSTRACT

A medical infusion pump includes a housing (10), a pump assembly (30), a bubble sensor assembly (120), a pressure sensor assembly (140) and a flow control assembly (180). The pump assembly includes a ring (26) with teeth (44) and a wheel (46) mounted for eccentric rotation within the ring. The pumping action is developed by the rotation of the wheel which continuously closes a portion of tubing (36) against one or two teeth as it goes through the pumping cycle. The bubble sensor includes a pair of sensor blocks (124) defining a generally V-shaped trough for cradling a portion of the tubing. The pressure sensor assembly detects pressure variations by movement of a diaphragm (168) coupled to a magnet (162) which is operatively coupled to a Hall effect circuit (160). The flow control assembly includes a thumb wheel (196) having a cam groove (197) interacting with a valve stem (199) for controlling the fluid flow through an orifice and associated valve seat (194).

12 Claims, 11 Drawing Sheets

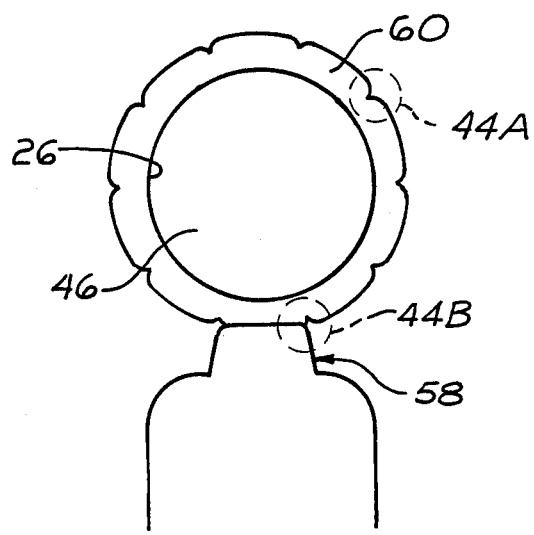
FIG. 3
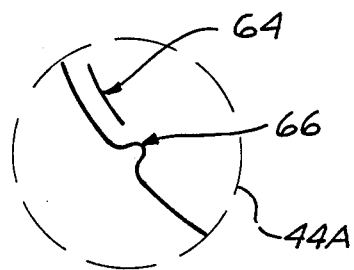 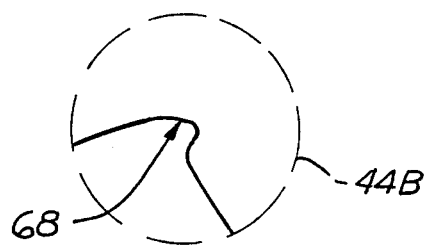
FIG. 4  FIG. 5

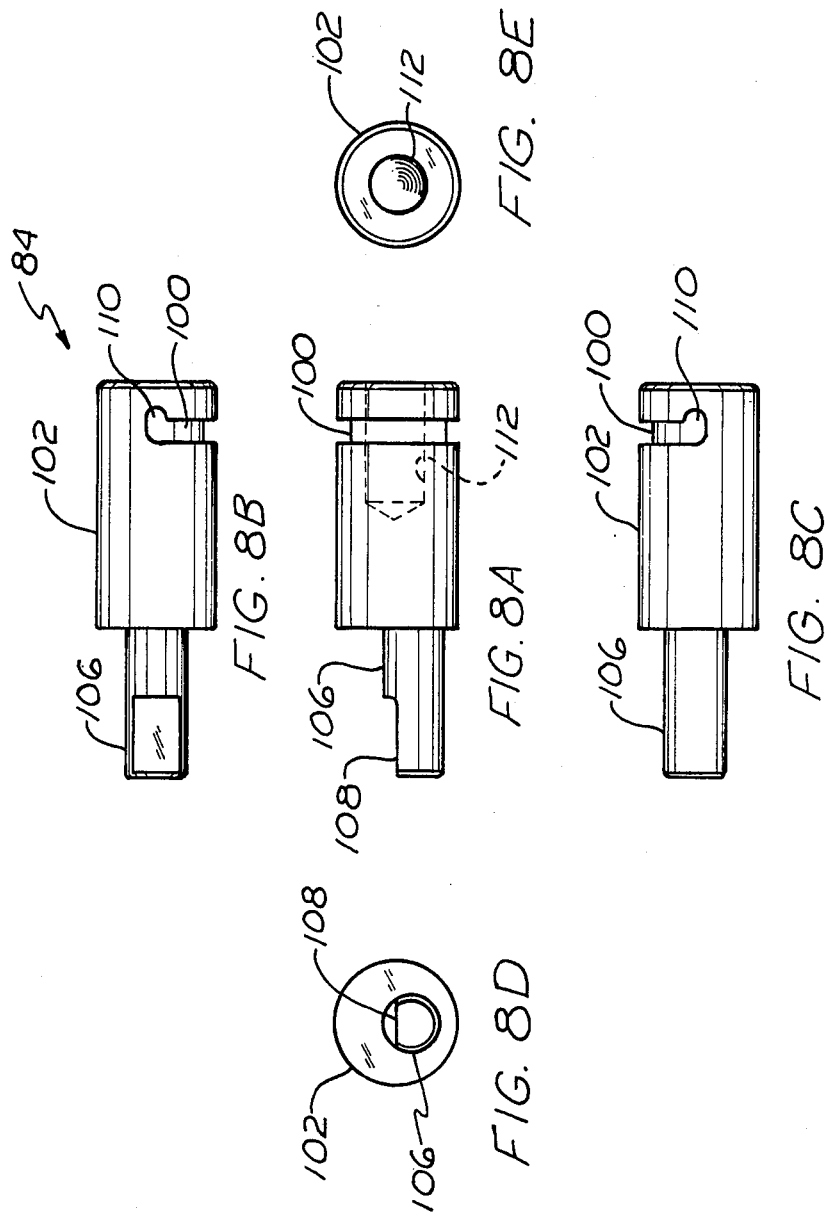

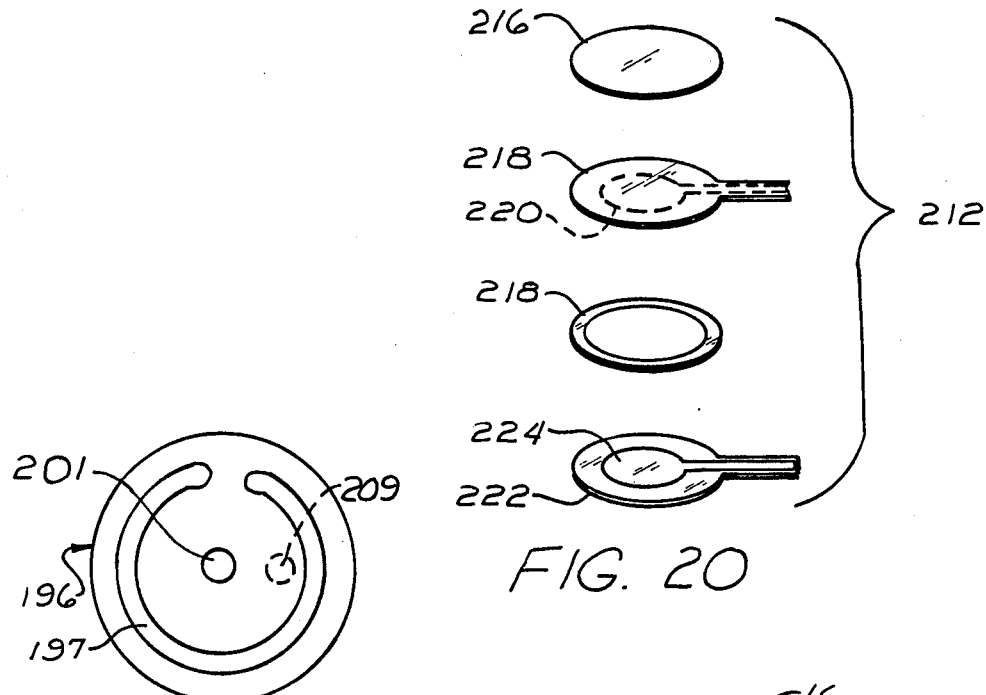
FIG. 19
FIG. 20
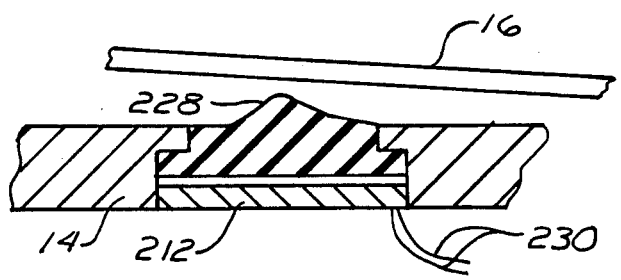
FIG. 21

MEDICAL INFUSION PUMP WITH SENSORS

BACKGROUND OF THE INVENTION

The present invention relates generally to fluid infusion systems, and more particularly to an improved medical infusion pump including several flow sensing devices.

The infusion of fluids into the human body is usually accomplished by means of an administration set in conjunction with a metering device which controls the rate of flow of fluid through the set. Peristaltic-type pumps, which function by repetitively compressing and expanding a section of tubing, have been frequently used since they do not introduce the possibility of leakage or contamination into the system while providing positive control of fluid flow through the system.

One such pump is described in U.S. Pat. No. 4,217,993 entitled "Flow Metering Apparatus for Fluid Infusion System". The patented pump construction includes individually spring-biased rollers in the pump rotor which provide a compression force to "squeeze" the fluid through the tubes in a pumping action. The metering apparatus disclosed in U.S. Pat. No. 4,217,993 includes a control system which allows the volume and rate of flow of the fluid to be infused to be preset by the operator. This control system provides an alarm function, in the event of malfunction of the pump or occlusion of the tubing of the administration set, and establishes a minimum pumping rate for maintaining fluid flow through the system after the desired volume of fluid has been infused. A bubble detector circuit is also described in U.S. Pat. No. 4,217,993. This detector comprises a multi-vibrator operatively connected to light generating and detecting components which compare the effects of bubbles in the fluid against a threshold value and sound an alarm when the threshold is exceeded.

Thus, the prior art in general teaches the use of a peristaltic infusion pump with associated sensors, but such apparatus known to date are not totally satisfactory.

Conventional peristaltic pumps have a reputation for excessive cell damage to fluid such as blood due to the continual strong compression of the inner diameter of the tubing contacted by the roller or equivalent structure. Also, such pumps often produce inaccuracies in the amount of fluid delivered because of small physical variations in the tubing introduced during manufacture, such as shore hardness variations, tubing symmetry, and variations in the relationship between the inner and outer diameters. Also, the heavy compression over an extended section of the tubing by the roller or equivalent structure often produces spalling, i.e., the flaking off of small particles of tubing after extended use.

Pressure sensors in conventional infusion pumps typically are either very expensive or are not sufficiently accurate. Typical low cost detectors have a measurement range of 4–8 psi plus or minus 4 or more psi.

Air-in-line, or bubble sensors are also known, but conventional sensors have had problems relating to repeatability of signal from administration set to administration set, and are characterized by inconvenience of inserting the tubing into the sensor device.

SUMMARY OF THE INVENTION

It is thus one object of the present invention to provide an economical system for infusing fluids into the human body with the flexibility and dynamic range to satisfy all of the demands of normal usage including pediatrics.

It is a more particular object to provide a peristaltic-type pump that will achieve the desired pumping action but not completely compress the walls of the tubing together to the extent that cells in the pumped fluid are damaged.

It is a further object of the invention to provide a peristaltic-type pump with which the pumping accuracy is minimally affected by physical variations in the administration set.

It is another object of the invention to provide an infusion pump having relatively inexpensive yet very accurate pressure sensors.

It is another object of the invention to provide an infusion pump having an accurate air-in-line sensor which can easily accommodate the administration set.

Finally, it is an object of the invention to provide a basic infusion pump to which sensors and other options can be added in a modular configuration.

In accordance with a complete embodiment of the invention, a medical infusion pump includes a housing, a pump assembly, a bubble sensor assembly, a pressure sensor assembly, and a flow control assembly, each having unique features which are operatively connected to each other for accomplishing all the objects recited above.

The housing includes a generally circular first cutout area defining a ring having spaced apart teeth projecting inwardly. The pump assembly is mounted in the housing and includes a wheel mounted for eccentric rotation within the first cutout such that the outer portions of the wheel sequentially compress a section of tubing circumferentially located between the wheel and the teeth, thereby providing a peristaltic-type action for pumping the fluid. When in the pumping mode, the wheel is offset relative to the center of the first cutout portion of the housing. A knob is provided on the wheel to selectively move the wheel into a centered position within the cutout, whereby the tubing can be inserted or removed from the housing.

In the preferred embodiment, the housing includes a second cutout area adjacent the first cutout area, for mounting various sensors and flow control devices. Preferably, the pressure sensor assembly is carried at least in part within a first cassette that is mountable in the second cutout portion adjacent the first cutout portion of the housing. The flow control assembly is contained within a second cassette that can interengage the first cassette to form a larger cartridge that is supported within the second cutout of the housing. A bubble sensor assembly is preferably mounted in the second cutout portion of the housing and is operable whether or not the pressure sensor cassette or flow control cassette is in place.

The bubble sensor includes a pair of sensor blocks defining a generally V-shaped trough for cradling a portion of the administration set tubing. An anvil, preferably located on a door or cover for the housing, is urged against the surface of the tubing that is not in contact with the sensor blocks, to slightly stress the tubing and thereby cause the portions of the tubing in contact with the blocks to be in substantially flat intimate contact. Ultrasonic transducers in each of the blocks are oriented substantially parallel to the tube surface in contact therewith. In this configuration the transducers can make accurate, repeatable measurements of the bubble content in the fluid passing through the tubing.

The pressure sensor assembly includes a cassette having a fluid chamber defined in part by a diaphragm. The diaphragm in the cassette is coupled to another diaphragm, preferably in the pump housing, for transmitting pressure variations that occur in the fluid chamber. The pressure variations are translated into linear movement of a magnet which in turn is operatively coupled to an integrated circuit which includes a Hall effect device. The movements of the magnet commensurate with the pressure variations in the fluid chamber are then manifested through the Hall effect circuit as a signal commensurate with pressure which may be employed to provide an indication to the operator or to energize an alarm.

The flow control assembly includes a second cassette having a body portion, a flow chamber within the body portion, a valve movable within the flow chamber to change the flow area therein, and a thumb wheel mounted on the body portion for engaging the valve to control valve movement and thus flow rate through the tubing. The valve preferably is mounted so that the default condition, when the door is open, is a no-flow condition. This eliminates undesired free flow to the patient, and assures that the second cassette can only be installed when the flow control valve is in the off position.

The invention as summarized above includes a variety of features which are preferably utilized together, but it should be understood that subcombinations of these features can fall within the scope of the invention in accordance with the appended claims.

BRIEF DESCRIPTION OF THE DRAWINGS

The above-discussed and other objects and advantages of the invention will be described in more detail below in connection with the description of the preferred embodiment and the accompanying drawings in which:

FIG. 3 is an enlarged view of the wheel in the centered position for insertion or removal of the tubing;

FIG. 4 is a detailed view of one tooth on the pump ring;

FIG. 5 is a detailed view of a tooth on the pump ring in the vicinity of the juncture of the first and second cutout regions;

FIG. 8a–8e are views of the secondary drive shaft of the pump assembly.

FIG. 19 is an elevation view of the thumbwheel component of the flow control cassette.

FIG. 20 is an exploded view of a membrane switch used in the preferred embodiment of the invention.

FIG. 21 is a substitute view of the door actuating a membrane switch.

DESCRIPTION OF THE PREFERRED EMBODIMENT

Figure 1:
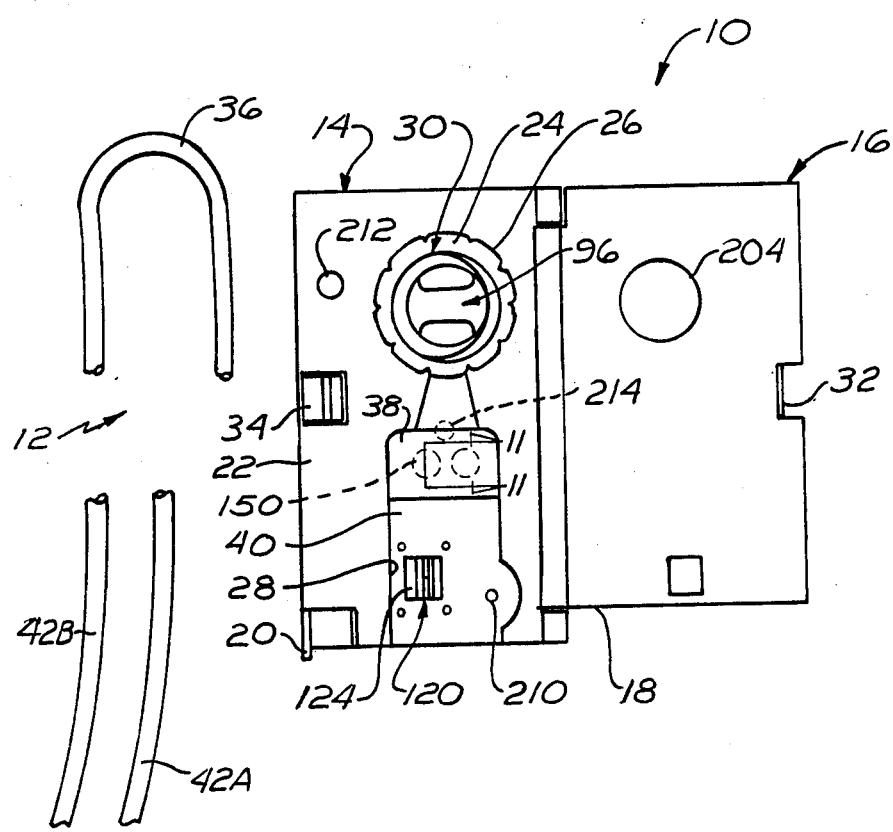
FIG. 1 is a front elevation view of an infusion pump apparatus and administration set in accordance with the complete implementation of the present invention.

FIG. 1 shows a medical infusion pump apparatus 10 and an associated administration set 12 through which fluids are infused into the patient including whole boood and packed RBC's. The pump apparatus includes a housing 14, a door 16 hinged at 18, and a lever 20. The face 22 of the housing includes two cutout areas. The first cutout area 24 has a substantially circular profile 26 and the second cutout area 28 has a generally rectangular profile located adjacent to the first cutout area. As will be more fully described below, the first cutout area 24 has a pump assembly 30 mounted therein and the second cutout area has sensor and control devices mounted therein. The door 16 preferably includes a catch area 32 for engagement with the latch 34. The lever 20 at the lower end of the housing is mounted for pivotal motion in a direction opposite that of the door 16 and draws the latch and door down tight to the housing 14.

As will be described in greater detail below, a cartridge assembly including the administration set 12, is placed within the pump apparatus 10. The administration set includes a pump tubing segment 36 which is connected to the upper portion of the cassette 38. Inlet or supply tubing 42a and delivery tubing 42b are connected to cassette 40. Preferably, cassette 38 and 40 are interengaged to form a unitary cartridge and the cartridge with the tubing 36, 42a, 42b connected thereto is inserted as an assembly into the pumping apparatus 10.

Referring also to FIGS. 2–7, the details of the pump assembly of the preferred embodiment will be described. In FIG. 2, the first cutout portion 24 of the housing includes a plurality of spaced apart teeth 44 projecting inwardly toward a circular wheel 46. The pump tubing segment 36 is interposed between the wheel and the teeth. The teeth may be formed in the wall of the housing defining the first cutout area, or they may be provided on a separate ring. For the purpose of this description, the pump ring will refer to that circular portion 26 of the housing wall defining the teeth.

Figure 2A:
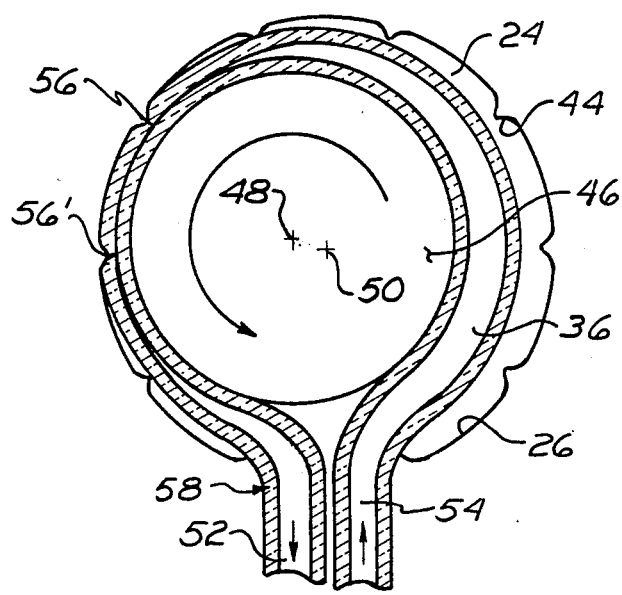
FIGS. 2a–2c are enlarged views of a portion of the pump assembly, including a wheel mounted for rotation within a circular cutout area of the housing, showing the wheel at several positions during the pumping cycle.
Figure 2B:
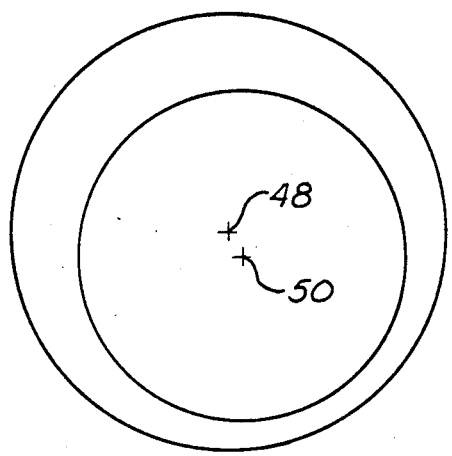
Figure 2C:
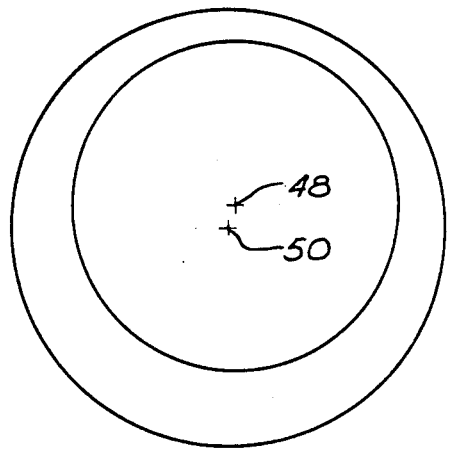

In a first position, the wheel center 48 is offset relative to the center 50 of the ring and, in addition, the wheel is mounted for eccentric rotation within the ring. FIGS. 2a–c show the wheel in three orientations during a full pumping cycle. FIG. 2a illustrates the wheel position as a quantity of fluid is pumped out of the tubing segment 36 at 52, FIG. 2b shows the wheel "trapping" a quantity of blood that has just entered the tubing at 54 in preparation for a peristaltic type transfer along the tubing, and in FIG. 2c, the wheel is shown at an intermediate position between those illustrated in FIGS. 2b and 2a.

The pump assembly of the present invention differs from that of conventional peristaltic pumps in that the wall of the tubing segment 36 is not completely compressed together except at small areas such as at 56 near the teeth 44. Backflow of blood is prevented by appropriately choosing the spacing and size of the teeth, as well as the relationship of diameters and eccentricity of rotation between the wheel and the pump ring. In particular, it is desirable that the portion of the wheel circumference farthest from the center 50 of the ring 26 continuously compress and close a portion of the tubing segment 36 against at least one tooth on the ring. When the farthest portion of the wheel circumference is midway between two teeth, the tube is under sufficient compressive deformation to be substantially closed at the lines of contact between the tubing and the two teeth, i.e. at the crowns of the teeth. For example, in FIG. 2a the tubing 36 is closed at 56 and 56'. Thus, when the wheel is in midposition between teeth, the wheel is closing the tubing against the two teeth on either side of it. The tubing is always closed against one or two teeth as it goes through the pumping cycle. The tubing between the teeth is never closed, nor do the walls of the tube between the teeth ever touch. It should be understood that the tube may not be closed at two teeth in the throat area 58 where the tubing segment 36 enters and leaves the first cutout area 24. In the illustrated embodiment, the pump tubing segment 36 substantially completely circumscribes the wheel 46, but the invention could be implemented in less preferred embodiments so long as at least about half of the wheel circumference is bordered by tubing.

FIG. 3 shows the wheel 46 in a centered position relative to the pump ring 26. In this second position, fluid cannot be pumped, but the tubing 36 may be inserted or removed from the space 60 between the ring and the wheel. Each of the wheel positions illustrated in FIGS. 2a–2c is a first position in that at least a portion of the wheel is in compressive engagement with the tubing, whereas in the wheel second position illustrated in FIG. 3, none of the tubing is compressively engaged by the wheel.

In the preferred embodiment, the speed of rotation of the wheel can be controlled to provide a more rapid rotation of the wheel during the portion of the pumping cycle where the extremity of the wheel passes between the positions shown in FIGS. 2a and 2b.

FIGS. 4 and 5 illustrate, in enlarged detail, the preferred shapes of the teeth 44 on the ring. Preferably ten teeth are provided in total, eight of a first type 44a and two of the second type 44b. All the teeth preferably have an apex 64 of about 0.025 inch, and a radius of curvature 66 at the apex of about 0.005 inch. The second type of teeth 44b are provided at the throat where the first cutout area joins the second cutout area. The radius of curvature 68 of the concave portion of these teeth is about 0.032 inch.

Figure 7:
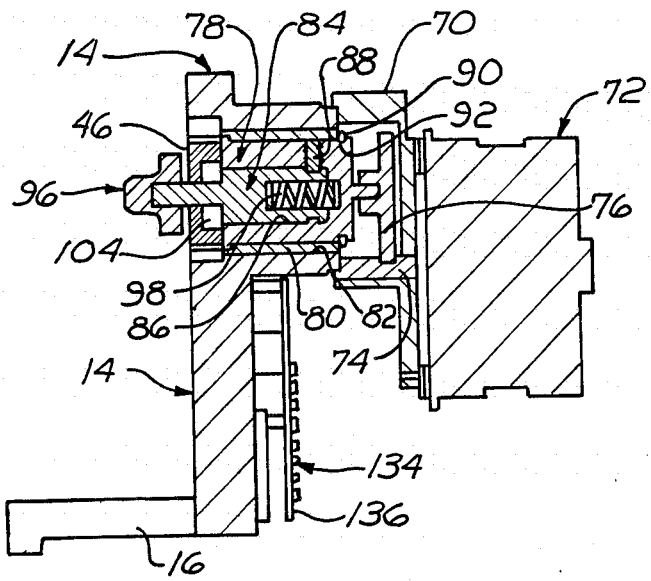
FIG. 7 is a side view, partly in section, taken along line 7—7 of FIG. 6.
Figure 6:
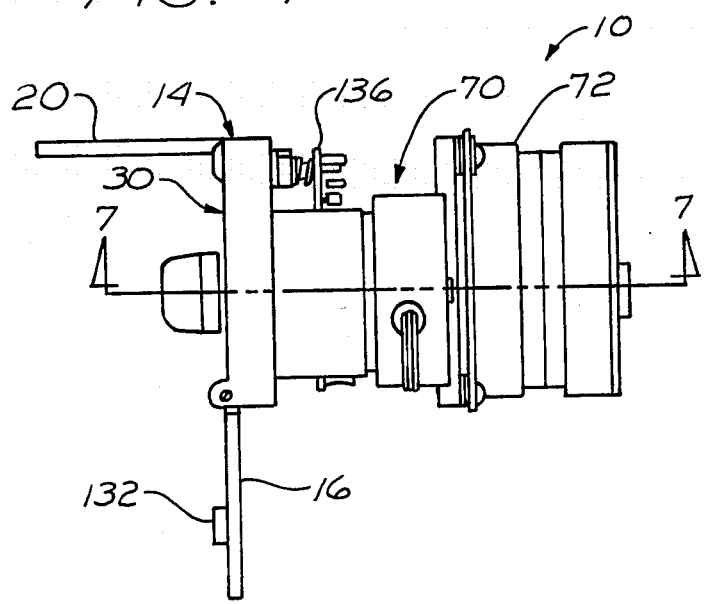
FIG. 6 is a top view of the housing and pump assembly shown in FIG. 1.
Figure 9:
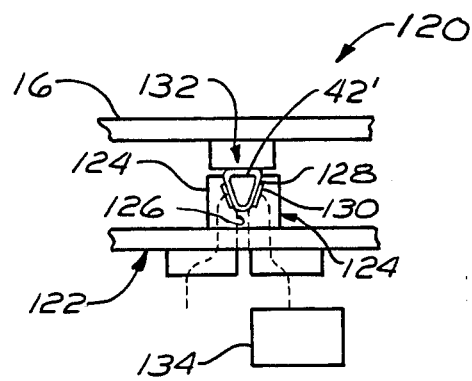
FIG. 9 is an elevation view of the air-in-line, or bubble sensor assembly.

With reference now to FIGS. 6 and 7, the preferred motor mount housing 70 of the pumping assembly 30 is shown for rotating the pump wheel 46. FIG. 6 is a top view of the pumping apparatus 10 of FIG. 1 (rotated 90 degrees), and FIG. 7 shows in section the drive shaft assembly for rotating the wheel. The pump drive stepper motor 72 has a pinion gear extension 74 which is coupled to a gear 76 providing a 5:1 reduction ratio. The gear 76 is attached to a primary drive shaft 78 which rides in a bearing 80 which is pressed into a bore 82 in the pump housing 14. The secondary drive shaft 84 is inserted within a bore 86 in the primary drive shaft 78 and held in place by a set screw 88. A retaining ring 90 is placed in a groove 92 which holds the primary shaft in the bearing. The pump wheel 46 rides on the secondary drive shaft 84 and is held in place by a knob 96. The secondary shaft is spring-loaded 98 in the outward direction relative to the primary drive shaft 78.

As shown in FIGS. 7 and 8, a groove 100 on the body portion 102 of the secondary drive shaft 84 cooperates with the set screw 88 in the primary shaft 78 to permit the secondary shaft to be selectively rotated 180 degrees by the knob 96, relative to the primary drive shaft. This moves the pump wheel 46 relative to the ring 26 in the pump housing 14 from the first position engaging the tubing, to the second position as shown in FIG. 3 for inserting and removing the tubing. A bearing 104 is inserted into a counter bore in the wheel, and mounted on the extension 106 of the secondary drive shaft. The extension axis is, however, offset relative to the axis of the body 102. As shown in FIGS. 2a–c, the pumping action is developed by the wheel pinching off the pump tubing against the teeth on the pump housing and then the offset rotation of the wheel causes this pinching off point to move along the tubing, forcing fluid to be moved, or pumped.

The knob 96 is attached to the end 108 of the secondary drive shaft and, although its primary purpose is to facilitate insertion and removal of the tubing in the pump assembly, the knob can also be used during a standby mode to allow the nurse the check the patency of the intravenous site by rotating the knob in the reverse direction, causing fluid to be moved backwards in the administration set.

As shown in FIG. 8, the groove 100 preferably spans one-half the circumference of the body portion 102, and includes a rearwardly extending J-type opening 110 at both extremities of the groove. The bore 112 is adapted to receive spring 98. Thus, during normal pump operation the spring bias causes the set screw to engage one of the openings 110, whereas pushing the knob 96 inward and rotating it causes the set screw to ride the groove 100 until it reaches the other opening 110.

The pump according to the present invention minimizes cell damage during the pumping action, and is relatively insensitive to small physical variations in the pump tubing segment such as shore hardness, tubing symmetry, and variations in the relationship of the inner and outer diameters. Preferably, the pump tubing segment 36 is made of silicon whereas the tubing 42 is made of PVC. Also, by repeatedly closing off the tubing only in the area close to the teeth of the pump, the problem of spalling has been greatly reduced.

With reference to FIGS. 1, 6, 7, and 9, the improved air-in-line or bubble sensor assembly 120 of the present invention, will be described in detail. Preferably, the air sensor device is mounted in the second cutout area 28 of the housing. The air sensor assembly includes a base portion 122 preferably constituting a portion of the pump housing 14, and a pair of sensor blocks 124 mounted in the base having inner walls 126 defining a trough 128 for supporting a portion of tubing 42' on two side surfaces. In the preferred embodiment, the tubing would be a portion of the administration set delivery tubing 42b, but this is not necessary. The side walls of the blocks are preferably flat and define a generally V-shaped trough therebetween forming an angle preferably about 30 degrees for cradling the tube.

Piezoelectric elements 130 are located within the sensor blocks 124 such that the transducers are in the flat inner walls and positioned to emit and receive sound waves perpendicularly through the side surfaces of the tube segment 42'. The accuracy and repeatability of measurements rely on a repeatable orientation of the tube relative to the transducers. With the present invention, the tube side walls are urged into a flat, intimate conforming relationship with the block inner walls, by the application of a slight compressive load on the upper surface of the tubing segment. Preferably, at least one half the tubing circumference is in contact with the block walls. In the illustrated embodiment, the upper portion of the tubing segment is compressed by a flat anvil 132 carried by the door 16 such that when the door is closed, a slight compressive stress is applied to the tubing so that it will conform to the shape of the trough. The presence or absence of fluid is detected by the magnitude of sound transmission through the tubing with lower transmission rates indicating the presence of air in the tubing. The transducer per se is conventional, typically utilizing an ultrasonic frequency of about 1.2 MHZ.

The present invention significantly increases repeatability of signal from administration set to administration set. Unlike conventional air sensors, which squeeze the tubing between flat upright blocks which create a "dog bone" shape in the tubing, the present invention consistently produces flat, even surfaces at the innerface between the transducer and the tubing.

As shown in FIG. 7, the electronics 134 associated with the air sensor are carried behind the housing face, in a printed circuit board 136. Other variables relating to the infusion of fluid into the patient are also monitored and displayed to the operator through the sensor assemblies to be described below which are also connected to the electrical components and circuit board shown in FIG. 7.

Figure 10:
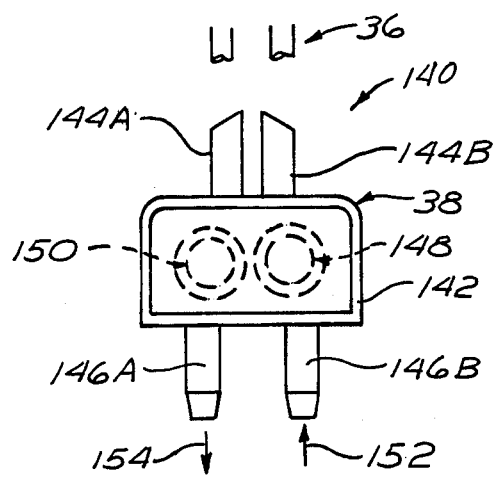
FIG. 10 is a top view of the pressure sensor assembly cassette.

The pressure sensor assembly 140 is preferably in the form of a cassette 38 as shown in FIGS. 1 and 10. The cassette 38 includes a body portion 142 adapted to mate with a portion of the recessed profile of the second cutout area 28, and fluid path connecting structure 144, 146 for connecting to the pump tubing segment 36 and either the other administration set tubing 42 or another cassette 40 that provides additional features. In the preferred embodiment, the pressure sensor cassette 38 includes two diaphragms 148, 150, shown in phantom, one for sensing the negative pressure in the inlet direction 152 and the other for sensing the pressure in the outlet direction 154.

Figure 11A:
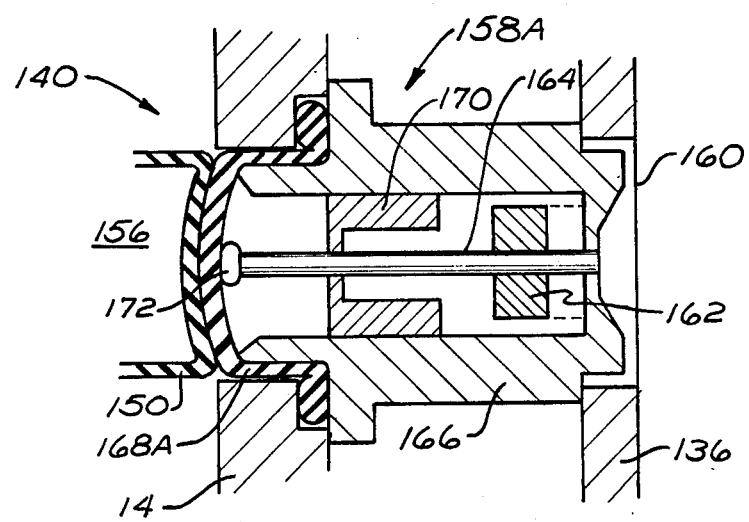
FIGS. 11a and 11b are sectional views of the pressure sensor assembly, including the pressure sensor cassette and the transducer and Hall effect circuitry mounted in the housing, FIG. 11a illustrating the preferred arrangement for sensing an increase in fluid pressure and FIG. 11b illustrating the preferred arrangement for sensing a decrease in fluid pressure.

FIGS. 11a and b are views taken along line 11—11 in FIG. 1 in a direction perpendicular to the plane of the drawing, and illustrate the basic features of the inventive pressure sensor assembly 140. FIGS. 10–16 illustrate the details of the preferred embodiment of this feature of the invention. The fluid line 144a connected to the pump and the outlet line 146a have interposed therebetween a fluid chamber 156. The chamber is defined in part by a first diaphragm 150 having a flexure response compatible with the range of pressures to be measured in the chamber. The first, or cassette diaphragm 150, is arranged to face a transducer assembly 158 preferably mounted in the housing. Thus, the cassette diaphragms are normally not visible to the operator.

Figure 11B:
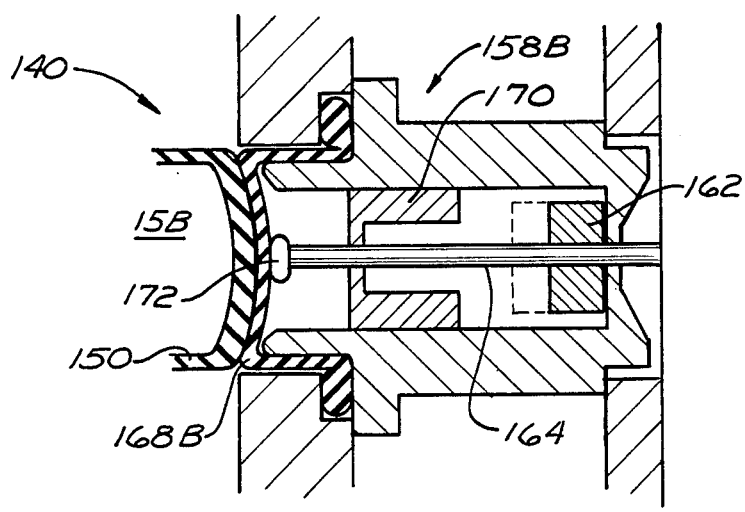
Figure 13:
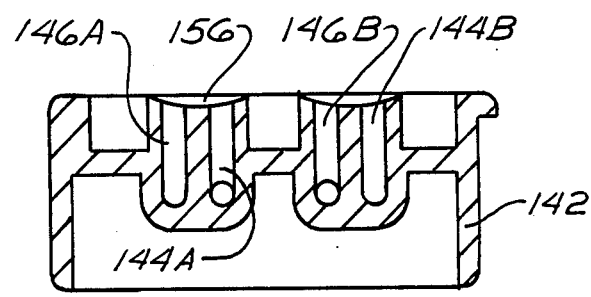
FIG. 13 is an elevation view in section taken along line 13—13 of FIG. 12.
Figure 12:
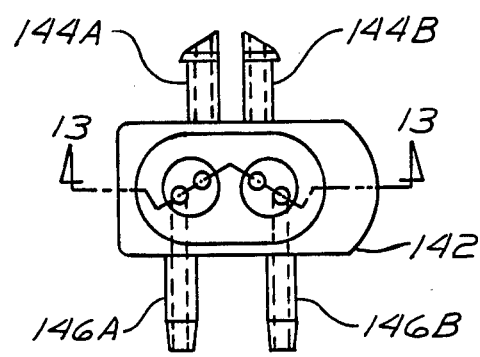
FIG. 12 is a bottom view of the pressure sensor cassette of FIG. 10, with the diaphragms removed.

Each diaphragm 150 has associated with it a transducer assembly 158, as shown in FIGS. 11a and 11b. Transducer assembly 158a is associated with the output flow through tubing 144a, 146a and the transducer assembly 158b is associated with the input flow through tubing 144b, 146b. The transducer assemblies include a Hall effect integrated circuit 160 spaced from the cassette diaphragm 150, a magnet 162 adjacent the integrated circuit, and rigid connecting means 164 between the magnet and the cassette diaphragm for producing a displacement of the magnet commensurate with the displacement of the diaphragm, thereby generating a signal in the Hall effect circuit indicative of the fluid pressure in the fluid chamber. Preferably, an outer bushing 166 is connected between the printed circuit board 136 and the face of the pump housing (see FIG. 7). A second, or sensor diaphragm 168, is in mating relationship with the cassette diaphragm 150. The connecting means 164 is preferably in the form of a thin brass translator pin adapted at one end to engage or hold the magnet 162 and at the other end to contact or engage the sensor diaphragm 168 for linear movement therewith. A second metal bushing 170 is provided within the first bushing for aligning the nose 172 of the pin against the sensor diaphragm.

Figure 14:
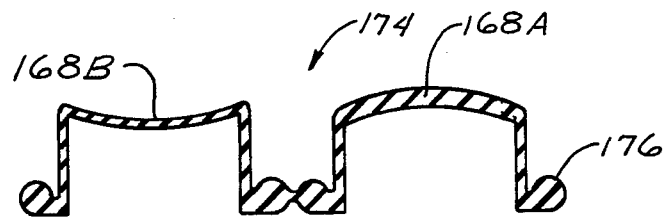
FIG. 14 is a sectional view of the dual cassette diaphragms for the pressure sensor cassette.

As shown in FIGS. 11 and 14, the input and output sensor diaphragm have different shapes. The output side diaphragm in FIG. 11a is normally contoured outwardly toward the cassette diaphragm and the input side diaphragm is contoured inwardly away from the cassette diaphragm. The purpose of these differences in contour is to eliminate stretching of the rubber diaphragms during a full range of sensing movement. The sensor diaphragms deform toward a substantially vertical or flat profile as the movement in the sensing direction increases, thus having sufficient material to allow a range of travel of approximately 0.050 inches without stretching the rubber.

Figure 16:
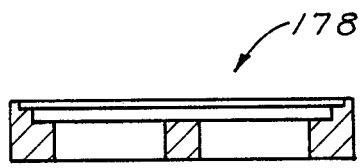
FIG. 16 is a sectional view of the diaphragm cover bracket for the pressure sensor cassette.
Figure 15:
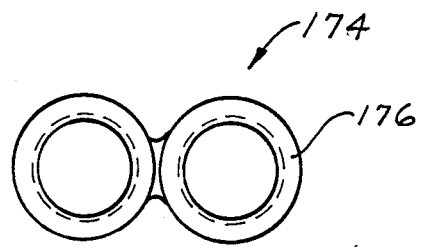
FIG. 15 is a top view of the diaphragms of FIG. 14.

The dual diaphragm 174 shown in FIGS. 14 and 15 is a molded silicon rubber part and incorporates O-rings 176 to seal the fluid path. A locking bracket 178, shown in FIG. 16, is preferably ultrasonic welded to the cassette body to hold the dual diaphragm in place. FIG. 14 shows the differences in shape of the output and input side diaphragms 168a, 168b, respectively. Preferably, the output side diaphragm wall is about twice as thick as the input side wall, with both diaphragms having approximately the same radius of curvature.

The pressure sensor assembly 140 of the present invention can resolve pressures to 0.05 psi, due in large part to the transducer arrangement that permits the use of a Hall effect integrated circuit. A satisfactory Hall effect circuit is available from the Microswitch Division of the Honeywell Company.

Figures 17, 18:
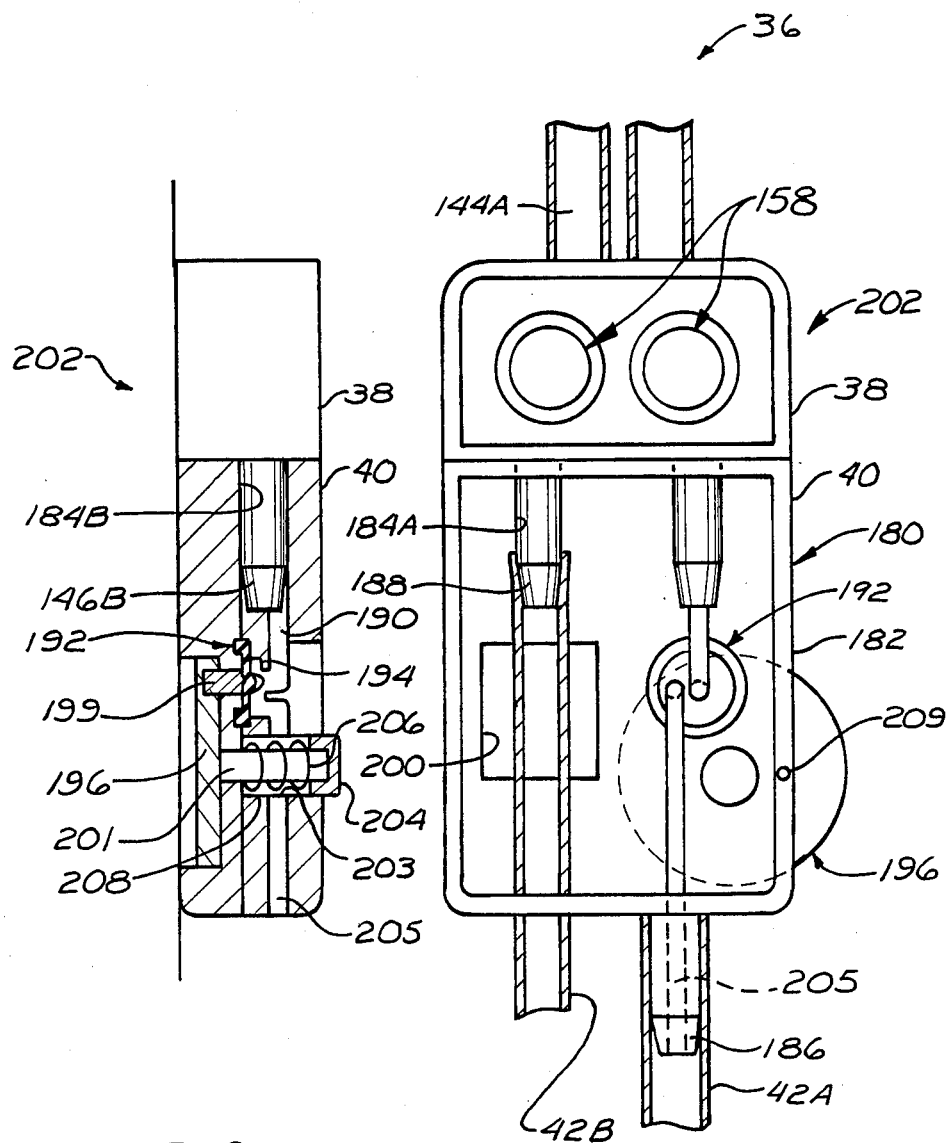
FIG. 17 is a plan view of the pressure sensor cassette and flow control cassette joined together to form a cartridge insert for the housing.
FIG. 18 is a side view, partly in section, of the flow control cassette; .

FIGS. 17–19 illustrate the preferred embodiment of the flow control assembly 180 of the present invention, which is in the form of a second cassette 40 adapted for modular engagement with the pressure sensor cassette 38 shown in FIG. 10. The flow control assembly has a body portion 182 having a pair of upper nozzle receptors 184a, 184b sized for interengagement with the lower nozzles 146a, 146b of the first cassette, and lower inlet 186 and outlet means 188 for fluidly connecting the ends of the administration set 42 to the flow control cassette. The flow control function is accomplished as shown in FIG. 18, wherein a flow chamber 190 is formed within the body part and a silicon valve 192 is located within the flow chamber in a position to control the flow orifice at valve seat 194 from a fully opened to a fully closed condition. The valve 192 is coupled to a thumb wheel 196 so that rotation of the thumb wheel causes the valve to open or close the orifice.

FIG. 19 is a plan view of the thumb wheel 196, showing the face containing a cam groove 197 which engages the stem 199 on the valve 192. The cam groove is sloped so that as the thumb wheel is rotated about its axis, the valve stem is pushed toward or away from the valve seat 194. The thumb wheel shaft 201 is mounted within a bore 203 in the body of the cassette, offset from the inlet flow path 205. A button 204 is slideably mounted within the bore and projects outwardly from the body of the cassette 40. A coil spring 206 is disposed in the bore between the button and a stop surface 208 in the cassette body. The spring biases the thumb wheel 196 towards the cassette body such that the valve 192 is normally in the closed position. Rotation of the thumb wheel permits a controlled flow rate through passage 190. The button 204 may be pushed at any time for instant full flow, and this feature is used primarily for purging the air from the set.

With further reference to FIG. 1, an additional feature of the present invention will be described. A hole 209 in the surface of the thumb wheel facing the cutout portion of the pump apparatus, is located so that it will mate with a boss 210 projecting from the cutout portion of the pump apparatus. This mating occurs only in the off position of the valve 192. The pump door 16 cannot be closed when the cassette valve 192 is in the on position, because the boss 210 will not engage the hole 208.

FIG. 1 also shows two membrane switches 212, 214. The first switch 212 signals the electronics that the door 16 is in the closed position and that the pump 30 and cartridge 202 are ready and in proper position. The other switch 214 senses a small appendage (not shown) on the pediatrics cassette 38. Actuation of second switch 214 sends a signal to the controller whereby the normal infusion rates and volumes are scaled down to levels appropriate for children. Thus, the operator is not called upon to alter settings in the unit for the pediatrics mode, but merely selects the proper infusion set and installs it.

FIG. 20 illustrates a preferred form of each membrane switch in which four components are stacked together. An adhesive wafer 216 with a paper backing is joined to a mylar base member 218 which carries a switch circuit 220 on its underside. Similarly, a mylar base member 222 having a switch circuit 224 on its upper surface is located below the first mylar member 218. A mylar spacer interposed therebetween. As shown in FIG. 21, when the door 16 contacts a silicon rubber disk 228 mounted in the housing 14, the disk 228 is depressed, making contact with the membrane switch 212 and causing the opposed circuit portions 220, 224 to make contact and thereby generate a control signal through wires 230.

As shown in FIGS. 1 and 17, in the preferred embodiment the second cassette 40 mates with the profile of the lower portion of the second cutout area 28 of the housing. When used with the preferred air sensor assembly 120 as described above, the second cassette 40 preferably includes a hole 200 located to permit the sensor blocks 124 shown in FIG. 9 to project upwardly therethrough, whereby the administration set tubing 42 connected to the nozzle receptor 184a or outlet 188 lies in the trough of the air sensor assembly.

Those skilled in this field can appreciate the benefit associated with the individual features of the invention as well as the flexibility afforded by combinations thereof. The pump assembly can be used alone or with other sensor devices. Preferably, in a low cost system, the pump assembly 30 is used with the air-in-line sensor assembly 120 and the pressure assembly 140 of the present invention. In a more complete system, the flow control cassette 40 is connected to the pressure sensor cassette 38, as shown in FIG. 18 and the resulting cartridge 202 is located within the profile of the second cutout area of the housing. The cartridge 202 having both the pressure sensing cassette and the flow control cassette may be used as a standard gravity set assembly without actuation of the pump, if desired.

The structural features of the invention having been set forth, the technique for operation will now be described with reference to FIG. 1.

The door 16 is opened by rotating the latch 32 away from the pump housing 14 and swinging the door outward. The pump knob 96 is grasped and pushed in as far as it will go, then rotated to the left. This centers the pump wheel 46 within the ring 26, away from the pump teeth 44, to provide clearance for the installation of the silicon pump tubing segment 36. The upper inlet and upper outlet nozzles 144a, 144b of the first cassette 38 are connected to the ends of the pump tubing segment 36. The second cassette 40 is then connected to the first cassette 38. The tubing 42a and 42b is connected to the second cassette 40. The complete cartridge unit is then placed in the first and second cutout areas of the pump housing. When the pump tubing is properly aligned between the wheel 46 and the pump ring 26, the knob 96 is pushed in as far as it will go and rotated to the right to urge the wheel into compressive engagement with the tubing. The door 16 is closed over the cutout areas and the lever 20 rotated to the right. In a preferred embodiment, the door has another circular hole 204 sized and located such that the door will not close unless the knob 96 is in the first position for pumping fluid.

I claim:

1. A medical infusion pump for receiving fluid through an administration set inlet tube and discharging fluid through an administration set delivery tube, comprising:
    (a) a housing, the housing including
        (1) means defining a generally circular first cutout area having first wall means defining a first profile including a plurality of spaced apart teeth projecting inwardly therefrom,
        (2) means defining a second cutout area adjacent said first cutout area, having second wall means defining a second profile,
    (b) a pump assembly mounted in said housing and including
        (1) a wheel having a peripheral surface, said wheel being mounted within said first cutout area, (2) administration set tubing comprising an inlet tube, a delivery tube and a tube segment interposed between said wheel and said first wall means, said segment fluidly connected to said inlet tube and said delivery tube, (3) means for selectively moving the wheel to a first position wherein a portion of said peripheral surface of the wheel compresses a portion of said tube segment against at least one of said teeth in said first wall means, and a second position wherein the wheel is spaced from said first wall means sufficiently to permit removal and replacement of the tube segment from between the wheel and said first wall means, (4) means for rotating the wheel eccentrically within the first wall means when the wheel is in the first position, such that said tube segment receives fluid from the inlet tube and the fluid is pumped through the tube segment by a peristaltic type action into the delivery tube;

(c) a bubble sensor assembly mounted on said housing for measuring changes in the air bubble content of the fluid in one of said inlet or delivery tubes, including (1) a pair of sensor blocks defining a generally V-shaped trough for cradling the sides of said tube, (2) an ultrasonic transducer in each of the blocks, oriented substantially parallel thereto toward the sides of the tubes, and (3) means for applying a slight pressure on the upper surface of the tubing along the portion thereof above the trough, whereby the portions of the tubing in contact with the blocks are held in substantially flat contact therewith during operation of the ultrasonic transducer;

(d) a pressure sensor assembly including (1) a first cassette removably located in said second cutout and including a fluid chamber in fluid communication with one of said tubes and a cassette disphragm responsive to the pressure in said chamber; and (2) a Hall effect sensor assembly including a movable magnet mounted in said housing and means in contact with said cassette diaphragm for translating movement of the cassette diaphragm into movements of said magnet commensurate with the pressure in said fluid chamber; and (e) a flow control assembly including a second cassette removably located in said second cutout area and means for providing fluid communication with at least one of said tubes and said first cassette, said second cassette including, (1) a body portion, (2) a flow chamber including an orifice in said body portion, (3) a valve movable within the flow chamber to change the flow area of the orifice, and (4) a thumb wheel mounted on the body portion and engaging the valve for controlling the flow area of the orifice.

2. The infusion pump of claim 1 wherein said bubble sensor assembly is mounted in said second cutout area.

3. The infusion pump of claim 2, wherein said pump assembly further includes a door for covering said first and second cutout areas.

4. The infusion pump of claim 3 wherein said door includes said means for applying a slight pressure on the tubing, such that the pressure is applied when the door is closed.

5. The infusion pump of claim 1 wherein said first cassette has a profile which mates with the portion of said second profile that is adjacent said first cutout area.

6. The infusion pump of claim 1 wherein said second cassette is engaged with said first cassette to form a unitary cartridge having a profile that mates with the profile of said second cutout area.

7. The infusion pump of claim 6 wherein at least one of said tubes passes through said second cassette and said second cassette includes an opening through which said bubble sensor assembly penetrates said second cassette when the second cassette is placed in said second cutout area, such that a portion of tubing passing through said second cassette is cradled in the trough of said bubble sensor assembly.

8. The infusion pump of claim 1 wherein said tubing segment is in the form of a piece of silicon tubing looped around said wheel and wherein, said first cassette has upper inlet and outlet nozzles and lower inlet and outlet nozzles, one end of said silicon tubing being connected to said upper inlet nozzle and the other end of said silicon tubing being connected to said upper outlet nozzle;

said second cassette has a pair of upper nozzle receptor means sized for interengagement and fluid communication with said lower nozzles on said first cassette, and lower inlet means for fluid connection to the inlet tube of said administration set and lower outlet means for fluid connection to the delivery tube of said administration set.

9. The infusion pump of 8 wherein said flow chamber of said second cassette is fluidly connected between said lower inlet means and one of said upper nozzle receptor means.

10. The infusion pump of claim 7 wherein said lower outlet means in said second cassette is adjacent said opening, such that when said delivery tube is connected thereto, a portion of the delivery tube is cradled by said bubble sensor assembly.

11. The medical infusion pump of claim 3 further including switch means on said housing for generating a control when said door is closed to properly cover said first and second cutout areas.

12. The medical infusion pump of claim 6 further including switch means in said second cutout area for generating a control signal when said cartridge is properly located in said second cutout area.

* * * * *